US011013834B2

(12) United States Patent
Lin

(10) Patent No.: US 11,013,834 B2
(45) Date of Patent: May 25, 2021

(54) HYDROPHILIC COATING FOR INTRAVASCULAR DEVICES

(71) Applicant: KONINKLIJKE PHILIPS N.V., Eindhoven (NL)

(72) Inventor: Tung-Liang Lin, Escondido, CA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 16/737,311

(22) Filed: Jan. 8, 2020

(65) Prior Publication Data

US 2020/0139019 A1 May 7, 2020

Related U.S. Application Data

(63) Continuation of application No. 15/148,001, filed on May 6, 2016, now Pat. No. 10,532,133.

(Continued)

(51) Int. Cl.

| | |
|---|---|
| ***A61L 31/10*** | (2006.01) |
| ***A61L 31/04*** | (2006.01) |
| ***A61L 29/04*** | (2006.01) |
| ***A61L 29/08*** | (2006.01) |
| ***A61B 5/0215*** | (2006.01) |
| ***A61B 5/026*** | (2006.01) |

(Continued)

(52) U.S. Cl.

CPC .............. *A61L 31/10* (2013.01); *A61B 5/026* (2013.01); *A61B 5/0215* (2013.01); *A61B 5/02158* (2013.01); *A61B 5/6851* (2013.01); *A61B 8/12* (2013.01); *A61L 29/041* (2013.01); *A61L 29/049* (2013.01); *A61L 29/085* (2013.01); *A61L 29/145* (2013.01); *A61L 31/041* (2013.01); *A61L 31/048* (2013.01); *A61L 31/145* (2013.01); *A61B 2562/12* (2013.01); *A61L 2400/10* (2013.01); *A61L 2420/02* (2013.01); *A61L 2420/06* (2013.01); *A61L 2420/08* (2013.01)

(58) Field of Classification Search

CPC ...... A61L 29/085; A61L 31/10; A61L 31/048; A61L 31/145; A61L 29/041; A61L 31/041; A61B 5/6851; A61B 8/12

See application file for complete search history.

(56) References Cited

U.S. PATENT DOCUMENTS 5,125,137 A 6/1992 Corl
5,243,988 A 9/1993 Sieben (Continued)

OTHER PUBLICATIONS

US 5,106,476 A, 08/2000, Corl (withdrawn)

*Primary Examiner* — Steve Rowland

(57) ABSTRACT

The present disclosure relates to a coating for medical devices. The lubricious coating includes a primer layer and a top coating layer as well as methods of making and using the same. The primer layer includes a reaction cured product of a multifunctional acrylate and an acid functionalized monoacrylate. The top coating layer includes a reaction cured product of a mixture that includes a hydrophilic polymer comprising polyvinylpyrrolidone, an acid functionalized monoacrylate, and a hydrophilic monomer. The lubricious coating may be coated onto medical devices to form a sensing guide wire, an ultrasound imaging device, and an intravascular imaging device. Associated devices and methods are also provided.

31 Claims, 9 Drawing Sheets

Related U.S. Application Data

(60) Provisional application No. 62/158,955, filed on May 8, 2015.

(51) Int. Cl.

| | |
|---|---|
| ***A61B 8/12*** | (2006.01) |
| ***A61B 5/00*** | (2006.01) |
| ***A61L 31/14*** | (2006.01) |
| ***A61L 29/14*** | (2006.01) |

(56) References Cited

U.S. PATENT DOCUMENTS 5,546,948 A 8/1996 Hamm
5,873,835 A 2/1999 Hastings
6,017,577 A * 1/2000 Hostettler .............. C08J 7/0427 427/2.12
6,221,425 B1 * 4/2001 Michal .................... C08L 89/00 427/2.25
6,551,250 B2 4/2003 Khalil
6,776,763 B2 8/2004 Nix
7,226,417 B1 6/2007 Eberle
8,104,479 B2 1/2012 Glynn
2003/0204238 A1 * 10/2003 Tedeschi ................... A61F 2/90 623/1.11
2006/0193989 A1 * 8/2006 Wegner ................. C08L 51/003 427/402
2009/0041923 A1 * 2/2009 Lin ....................... A61L 29/085 427/2.3
2009/0155575 A1 * 6/2009 Dias ...................... A61L 29/085 428/335
2010/0114042 A1 * 5/2010 Dias ........................ A61L 31/10 604/265
2011/0200828 A1 * 8/2011 Li ........................... A61L 31/10 428/414
2012/0041545 A1 * 2/2012 Wyman ................. C08F 220/18 623/1.46
2012/0077049 A1 * 3/2012 Lin ......................... A61L 27/34 428/520
2013/0023758 A1 * 1/2013 Fabro ..................... A61B 6/481 600/424
2013/0123664 A1 * 5/2013 Lin ....................... A61L 29/041 600/585
2013/0136847 A1 * 5/2013 Lee ......................... A61L 29/16 427/2.3
2013/0323291 A1 * 12/2013 Li ........................... A61L 31/10 424/409
2014/0005543 A1 1/2014 Burkett
2014/0180141 A1 6/2014 Millett
2014/0187874 A1 7/2014 Burkett
2014/0187916 A1 * 7/2014 Clark ..................... A61B 5/062 600/424
2014/0187980 A1 7/2014 Burkett
2014/0187984 A1 7/2014 Burkett
2015/0217090 A1 8/2015 Burkett
2015/0352259 A1 * 12/2015 Rooijmans ......... C08G 65/3322 428/474.4
2016/0022215 A1 1/2016 Henderson
2016/0325024 A1 11/2016 Lin

* cited by examiner

HYDROPHILIC COATING FOR INTRAVASCULAR DEVICES

CROSS-REFERENCE TO RELATED APPLICATIONS

The present application is a continuation of U.S. application Ser. No. 15/148,001, filed May 6, 2016, now U.S. Pat. No. 10,532,133, which claims priority to and the benefit of U.S. Provisional Patent Application No. 62/158,955, filed May 8, 2015, each of which is hereby incorporated by reference in its entirety.

FIELD OF DISCLOSURE

The present disclosure relates to a lubricious coating for coating at least one section of a medical device, methods for the production and use of such lubricious coatings, and medical devices having such lubricious coatings. In several exemplary embodiments, the coating includes a primer layer to promote adhesion and a top coating layer to increase the lubricity of the surface of the medical device. The coatings disclosed herein may find application in medical devices such as intravascular ultrasound (IVUS) imaging catheters, guide wires, microcatheters, delivery systems, and ureteral stents, where high lubricity is desired for optimal performance. In some embodiments, medical devices such as sensing guide wires, ultra sound imaging devices, and intravascular imaging devices having such lubricious coatings are disclosed.

BACKGROUND

Intracorporeal medical devices such as guide wires and stents have revolutionized modern medicine by allowing medical care providers to insert cameras and mechanical devices into blood vessels and urinary tubes. These medical devices allow for blood vessels and urinary tubes to be imaged and treated without the need for more invasive surgical procedures. However, the insertion of these medical devices into blood vessels and urinary tracts can lead to abrasions on the inner surface of the vessels if the devices do not easily slide along the surface of the vessel walls. These scratches can cause a failure of the vessel walls or a thickening of the vessel walls that lead to constriction of the diameter of the vessel.

Lubricious coatings have been developed that provide the coated medical devices with a low coefficient of friction when the coating becomes wet. However, the development of lubricious coatings presents a different set of challenges due to the inherently high risks of device failure during invasive medical procedures. The coating must adhere strongly to the medical device, because if the coating were to delaminate, then the delaminated film could form a catastrophic blockage of a blood vessel. At the same time, the same coating must also provide a low adhesion, low friction surface on the exterior of the coating to avoid damaging the blood vessels that the medical device must move through.

Past efforts to develop lubricious coatings have been directed toward the development of interpenetrating networks (IPNs) that formed a first network of cross linked polymers in the presence of a second network of cross linked polymers to provide a coating having the adhesive properties of the first network along with the lubricious properties of the second network. See, for example, U.S. Patent Application Publication Nos. 2013/0123664, 2012/0077049, and 2009/0041923.

Despite these advances, there is a need for a coating that can adhere strongly to a section of a medical device while providing an exterior surface having high lubricity.

SUMMARY

A coating in contact with at least one section of a medical device is disclosed herein. In several exemplary embodiments, the coating includes: a primer layer including the reaction cured product of a first mixture and a top coating layer including a reaction cured product of a second mixture. In several exemplary embodiments, the first mixture includes: a multifunctional acrylate and a first acid functionalized monoacrylate. In several exemplary embodiments, the second mixture includes: a hydrophilic polymer including polyvinylpyrrolidone, a second acid functionalized monoacrylate, a hydrophilic monomer, and a second polymerization initiator. In several exemplary embodiments, the primer layer directly contacts the at least one section of the medical device. In several exemplary embodiments, the top coating layer is in contact with the primer layer and is an outermost layer of the coating.

A method of coating at least one section of a medical device is disclosed herein. In several exemplary embodiments, the method includes: applying a first mixture onto the at least one section of the medical device; curing the first mixture to form a primer layer in direct contact with the at least one section of the medical device; applying a second mixture into contact with the primer layer; and curing the second mixture to form a top coating layer; wherein the top coating layer is the outer most layer of the coating. In several exemplary embodiments of the method, the first mixture includes a multifunctional acrylate, a first acid functionalized monoacrylate, and a first polymerization initiator. In several exemplary embodiments of the method, the second mixture includes: a hydrophilic polymer including polyvinylpyrrolidone, a second acid functionalized monoacrylate, a hydrophilic monomer, and a second polymerization initiator.

Medical devices, such as intravascular devices, having lubricious coatings are disclosed herein. According to several exemplary embodiments, the intravascular device includes: a flexible elongate member, wherein at least a portion of the flexible elongate member includes an outer coating, the outer coating comprising: a primer layer comprising the reaction cured product of a first mixture comprising: a multifunctional acrylate, a first acid functionalized monoacrylate, and a first polymerization initiator; and a top coating layer comprising a reaction cured product of a second mixture comprising: a hydrophilic polymer comprising polyvinylpyrrolidone, a second acid functionalized monoacrylate, a hydrophilic monomer, and a second polymerization initiator; wherein the top coating layer is in contact with the primer layer and is an outermost layer of the coating. The flexible elongate member can be a guide wire and can include at least one sensing element, such as a pressure sensor and/or a flow sensor. The guide wire can have an outer diameter of about 0.014 inches, about 0.018 inches, about 0.035 inches, or other suitable size. The flexible elongate member can be a catheter and can include at least one imaging element, such as an ultrasound transducer.

BRIEF DESCRIPTION OF THE DRAWINGS

The following descriptions of the drawings are merely an embodiment of the disclosure and should not be considered limited. Also, the drawings are merely a depiction of embodiments and are not drawn to scale.

DETAILED DESCRIPTION

The term "about" indicates a range which includes ±5% when used to describe a single number. When applied to a range, the term "about" indicates that the range includes −5% of a numerical lower boundary and +5% of an upper numerical boundary. For example, a range of from about 100° C. to about 200° C., includes a range of from 95° C. to 210° C. A range of about 5:1 to about 1:5 includes a range of from 5.25:1 to 0.95:5. However, when the term "about" modifies a percentage, then the term means±1% of the number or numerical boundaries, unless the lower boundary is 0%. Thus, a range of 5-10%, includes 4-11%. A range of 0-5%, includes 0-6%.

Unless indicated otherwise, all measurements have metric units.

Unless indicated otherwise, the terms "a," "an," or "the" can refer to one or more than one of the noun they modify.

The phrase "section of a medical device" refers to a length of a medical device that will be exposed to the environment during intravascular medical procedures.

The term "multifunctional" or "functionalized" refers to an acrylate having two or more functional groups or one functional group, respectively, wherein the functional groups are non-hydrocarbon parts of the molecule, excluding the vinyl and carbonyl group of the acryl group, that are capable of reacting with other molecules. Suitable functional groups include alcohol groups, ester groups, carboxylic acid groups, amine groups, epoxide groups, aziridine groups, and the like.

The unit of measurement for the number average molecular weight can be interchangeably expressed as grams per mole or Daltons.

The term "acid functionalized monoacrylate" refers to an acid functionalized acrylate monomer or an acid functionalized acrylic oligomer.

Figure 1:
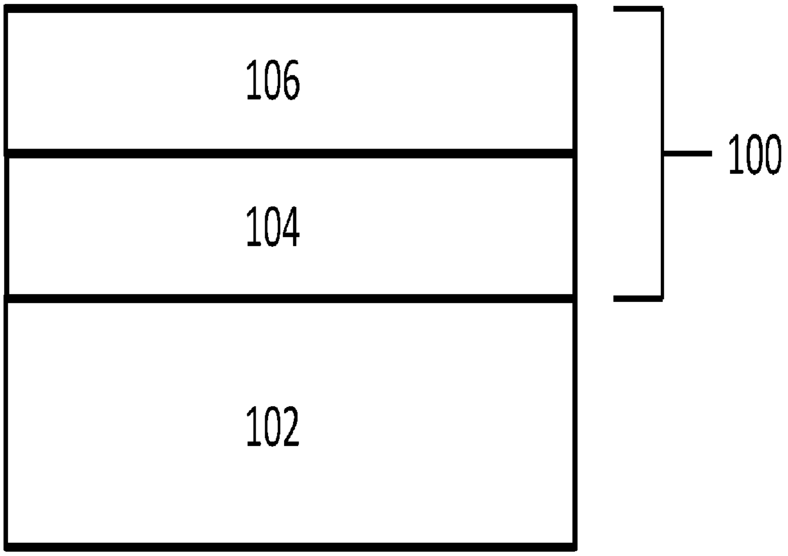
FIG. 1 schematically depicts an embodiment of a coating in contact with at least one section of a medical device.

Referring to FIG. 1, a coating 100 in contact with at least one section of a medical device 102 is disclosed herein. In several exemplary embodiments, the coating 100 includes a primer layer 104 and a top coating layer 106. In several exemplary embodiments, the primer layer 104 of the coating 100 directly contacts at least one section of the medical device 102. In several exemplary embodiments, the top coating layer 106 is an outermost layer of the coating 100 and is in direct or indirect contact with the primer layer 104.

In several exemplary embodiments, the primer layer 104 includes the reaction cured product of a mixture that includes a multifunctional acrylate, an acid functionalized monoacrylate, and a polymerization initiator. In several exemplary embodiments, the primer layer 104 has the function of promoting strong adhesion to the medical device 102. In several exemplary embodiments, the primer layer 104 mixture includes the multifunctional acrylate and the acid functionalized monoacrylate in a ratio of from about 5:1 to about 1:5, from about 3:1 to about 1:3, or about 1:1.

In several exemplary embodiments, the multifunctional acrylate is a network forming monomer that is capable of crosslinking the primer layer 104 to provide strength, improved cohesion, and insolubility to the primer layer 104. In several exemplary embodiments, the multifunctional acrylate is trimethylolpropane triacrylate (TMPTA) or trimethylolpropane ethoxylate triacrylates.

In several exemplary embodiments, the acid functionalized monoacrylate of the primer layer 104 mixture is an adhesion promoter. In several exemplary embodiments, the acid functionalized monoacrylate of the primer layer 104 mixture can include one or more of PHOTOMER® 4173, PHOTOMER® 4703, PHOTOMER® 4846, which are acid functionalized monoacrylates commercially available from IGM Resins.® In several exemplary embodiments, the acid functionalized monoacrylate of the primer layer 104 mixture is present in solution in a weight percentage of from about 0.1% to about 20.0% or from about 1.0% to about 5.0% based on the total weight of the primer layer 104 mixture. According to several exemplary embodiments, the second mixture can contain a UV curable or UV-C curable crosslinkers, where UV-C refers to the range of UV light extending from 100-190 nm.

In several exemplary embodiments, the top coating layer 106 includes a reaction cured product of a mixture that provides a lubricious surface on the outer most layer of the coating 100. In several exemplary embodiments, the top coating layer 106 includes a reaction cured product of a mixture that includes a hydrophilic polymer including polyvinylpyrrolidone, an acid functionalized monoacrylate, a hydrophilic monomer, and polymerization initiators. In several exemplary embodiments, the top coating layer 106 includes the polyvinylpyrrolidone and the acid functionalized monoacrylate in a mass ratio of from about 20:1 to about 30:1 or from about 22:1 to about 28:1.

In several exemplary embodiments, the hydrophilic polymer includes polyvinylpyrrolidone (otherwise known as PVP or poly(N-vinyl-2-pyrrolidone)). In several exemplary embodiments, the polyvinylpyrrolidone has a number average molecular weight of at least 900,000 g/mol or from about 900,000 g/mol to about 1,500,000 g/mol. A suitable example of polyvinylpyrrolidone is PVP K90, which is commercially available from Ashland Inc or BASF, and has a number average molecular weight of 1,300,000 g/mol. Benefits of the hydrophilic polymer include solubility in aqueous solutions, high lubricity when wet, and that the polymer is already polymerized to a known molecular weight distribution.

In several exemplary embodiments, the acid functionalized monoacrylate of the top coating layer 106 mixture is a monomer that polymerizes to bind the top coating layer 106 to the primer layer 104 and to immobilize the hydrophilic polymer in the top coating layer 106 and on the surface of the top coating layer 106. In several exemplary embodiments, the acid functionalized monoacrylate of the primer layer 104 mixture can include one or more of PHOTOMER® 4173, PHOTOMER® 4703, PHOTOMER® 4846, which are acid functionalized monoacrylates commercially available from IGM Resins.® In several exemplary embodiments, the acid functionalized monoacrylate of the top coating layer 106 mixture is present in solution at a weight percent of from about 0.01% to about 20.0% based on the total weight of polyvinylpyrrolidone in the top coating layer 106. In several exemplary embodiments, the acid functionalized monoacrylates of the primer layer 104 mixture and the top coating layer 106 mixture are independently selected and can be the same or different.

In several exemplary embodiments, the hydrophilic monomer is not generally limited, so long as the hydrophilic monomer is capable of free radical polymerization and is hydrophilic enough to not phase separate from the top coating layer 106 mixture. In several exemplary embodiments, the hydrophilic monomer includes 1-vinyl-2-pyrrolidone, N,N-dimethylacrylamide, and combinations thereof.

In several exemplary embodiments, the polymerization initiators are free radical initiators. In several exemplary embodiments, the polymerization initiator and the polymerization initiators of the primer layer 104 mixture and the top coating layer 106 mixture are independently selected and can be the same or different. The choice of polymerization initiator is not particularly limited so long as the polymerization initiator is soluble in the solvent used for polymerization and can initiate free radical polymerization. In several exemplary embodiments, the polymerization initiator includes a thermal initiator, a redox initiator, a photoinitiator, and combinations thereof. A suitable thermal initiator includes azobisisobutyronitrile (AIBN). Suitable redox initiators include potassium peroxydisulfate and ammonium peroxydisulfate. In several exemplary embodiments, the polymerization initiator is a photoinitiator. In several exemplary embodiments, the photoinitiator includes benzophenone, 2,2-dimethoxy-2-phenylacetophenone, and combinations thereof. In several exemplary embodiments, the polymerization initiator of the primer layer 104 mixture is present at a weight percentage of from about 0.001% to about 2.0% of the total weight of mixture, excluding the weight of any solvent used. In several exemplary embodiments, the polymerization initiator is of the top coating layer 106 mixture is present at a weight percentage of from about 0.001% to about 2.0% of the total weight of the top coating layer 106 mixture, excluding the weight of any solvent used.

In several exemplary embodiments, the structure of the coating 100 formed provides strong adhesion on the primer layer 104 side of the coating 100 and high lubricity on the top coating layer 106 side of the coating 100. Moreover, in several exemplary embodiments, the structure of the primer layer 104 and the top coating layer 106 provides strong adhesion and high lubricity, respectively.

In several exemplary embodiments, the structure of the primer layer 104 is highly cross linked due to the ratio of multifunctional acrylate, which is a cross linker, to acid functionalized monoacrylate, which is an adhesion promoter. In several exemplary embodiments, reaction curing the primer layer 104 in contact with at least one section of the medical device 102 provides a reaction cured product that is a highly cross linked copolymer of the multifunctional acrylate and acid functionalized monoacrylate. In several exemplary embodiments, the high number of cross links in the primer layer 104 provides strength and cohesion, whereas the high number of acid functionalized groups in the primer layer 104 provides strong adhesion to a section of the medical device 102.

In several exemplary embodiments, the structure of the top coating layer 106 is a non-cross linked copolymer composite. In several exemplary embodiments, the structure of the top coating layer 106 is a reaction cured product that is a non-cross linked copolymer of an acid functionalized monoacrylate and a hydrophilic monomer that immobilizes the hydrophilic polymer as a functional filler. In several exemplary embodiments, the weight percent of the hydrophilic polymer is more than 75% of the total weight of the top coating layer 106, and the lubricious properties of the hydrophilic polymer dominate the surface properties of the top coating layer 106. In several exemplary embodiments, the top coating layer 106 adheres to the primer layer 104 due to the presence of the relatively low amount of acid functionalized segments of the copolymer, but the adhesive properties of the acid functionalized segments of the copolymer are mitigated by the presence of the non-adhesive, hydrophilic segments of the copolymer. In this way, the top coating layer 106 has the highly lubricious properties of the hydrophilic polymer, which makes up most of the mass of the top coating layer 106, with enough copolymer to bind the hydrophilic polymer to the primer layer 104. Further, unlike in previous lubricious coatings, such as those disclosed in U.S. Patent Application Publication Nos. 2013/0123664, 2012/0077049, and 2009/0041923, the top coating layer 106 disclosed herein is not cross linked.

In several exemplary embodiments, the coating includes poly(N-vinyl-2-pyrrolidone), which is cross-linked by UV-C or a PVP crosslinker; a vinyl monomer; monoacrylate; an acid functional monoacrylate prepolymer; and a polyfunctional aziridine crosslinker.

In several exemplary embodiments, the medical device is not particularly limited so long as it is a medical device that would benefit from having a lubricious surface coating to avoid damaging vasculature. In several exemplary embodiments, the medical device includes a catheter, such as intravascular ultrasound (IVUS) imaging catheters or microcatheters; a guide wire; a delivery system; a stent, such as a ureteral stent; and the like. "Delivery system" means a delivery catheter or system which is used to deliver devices including a stent, a heart valve, or any implants.

In several exemplary embodiments, the medical device is a sensing guide wire that includes a flexible elongate member; a flexible element extending distally from the flexible elongate member; a core member extending within a lumen of the flexible element; the coating fills at least a portion of the lumen between the core member and the flexible element along a length of the flexible element; and a sensing element positioned distal of the flexible element.

In several exemplary embodiments, the medical device is a sensing guide wire that includes a flexible elongate member; a radiopaque element extending distally from the flexible elongate member, the radiopaque element being a variable pitch coil defining a first radiopaque section, a second radiopaque section, and a radiolucent section positioned between the first and second radiopaque sections; the coating fills at least a portion of a lumen of the radiopaque element along a length of the radiopaque element; and a sensing element coupled to the flexible elongate member.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guide wires and catheters. In that regard, catheters may or may not include a lumen extending along its length for receiving and/or guiding other instruments. If the catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a flow sensor, a temperature sensor, an imaging element, an optical fiber, an ultrasound transducer, a reflector, a mirror, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized.

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guide wire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm), approximately 0.018" (0.4572 mm), and approximately 0.035" (0.889 mm). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

A method for coating at least one section of a medical device is disclosed herein. In several exemplary embodiments, the method includes applying a mixture onto at least one section of the medical device to form a primer layer, wherein the mixture includes: a multifunctional acrylate, an acid functionalized monoacrylate, and polymerization initiators. The method of applying the mixture to a section of the medical device is not limited, so long as all of the components are brought together and applied directly to the section of the medical device. In several exemplary embodiments, the step of applying the mixture includes dipping, spraying, wiping, brushing, or molding the mixture onto a section of the medical device. In several exemplary embodiments, the method includes applying a pre-formed mixture directly onto the surface of the medical device. In several exemplary embodiments, the method includes applying each ingredient together or separately onto the surface of the medical device to form the primer layer by replacing the mixture in direct contact with the medical device.

In several exemplary embodiments, the mixture includes a multifunctional acrylate, an acid functionalized monoacrylate, a polymerization initiator, and a solvent. The solvent in the mixture is not limited so long as the solvent is polar and capable of dissolving the components of the mixture. Suitable solvents include water, methanol, ethanol, propanol, butanol, isopropyl alcohol, tetrahydrofuran (THF), acetone, and mixtures thereof and the like. In several exemplary embodiments, the solvent makes up about 92% to about 95% w/w of the mixture based on the total weight of the mixture. It is understood that the solvent can evaporate off when heated or allowed to dry to provide the cured primer layer 104.

In several exemplary embodiments, the method includes curing the mixture onto at least one section of the medical device. The method of curing the mixture is not limited, but will depend on the choice of polymerization initiator. In several exemplary embodiments, if the polymerization initiator is a thermal initiator, then the mixture is heated while in direct contact with a section of the medical device at a temperature of from about 40° C. to about 80° C. or from about 50° C. to about 70° C. for from about 10 minutes to an hour. In several exemplary embodiments, if the polymerization initiator is a photoinitiator, then the mixture is irradiated by a source of ultraviolet light (UV) for about 30 seconds to 10 minutes using, for example, a high pressure mercury arc lamp.

In several exemplary embodiments, the method includes applying a mixture onto the primer layer to form a top coating layer, wherein the mixture includes a hydrophilic polymer including polyvinylpyrrolidone, an acid functionalized monoacrylate, a hydrophilic monomer, and a polymerization initiator. The method of applying the mixture to the primer layer is not limited, so long as all of the components are brought together and applied directly or indirectly into contact with the primer layer of the coating. In several exemplary embodiments, the step of applying the mixture includes dipping, spraying, wiping, brushing, or molding the mixture onto a section of the medical device to which has been previously applied to a primer layer. In several exemplary embodiments, the method includes applying a preformed mixture into direct or indirect contact with the primer layer. In several exemplary embodiments, the method includes applying each ingredient onto the primer layer to form the mixture in contact with the primer layer.

In several exemplary embodiments, the mixture includes a hydrophilic polymer including polyvinylpyrrolidone, an acid functionalized monoacrylate, a hydrophilic monomer, a polymerization initiator, and a solvent. The solvent in the mixture is not limited so long as the solvent is polar and capable of dissolving the components of the mixture. Suitable solvents include water, methanol, ethanol, propanol, butanol, isopropyl alcohol, tetrahydrofuran (THF), acetone, and mixtures thereof and the like. In several exemplary embodiments, the solvent makes up about 92% to about 95% wt/wt based on the total weight of the mixture. It is understood that the solvent can evaporate off when heated or allowed to dry to provide the reaction cured top coating layer.

In several exemplary embodiments, the method includes curing the mixture onto the primer layer. The method of curing the mixture is not limited, but will depend on the choice of the polymerization initiator. In several exemplary embodiments, if the polymerization initiator is a thermal initiator, then the mixture is heated while in direct or indirect contact with the primer layer at a temperature of from about 40° C. to about 80° C. or from about 50° C. to about 70° C. for about 10 minutes to an hour. In several exemplary embodiments, if the polymerization initiator is a photoinitiator, then the mixture is irradiated by a source of ultraviolet light (UV) for about 30 seconds to 10 minutes using, for example, a high pressure mercury arc lamp.

Figure 3:
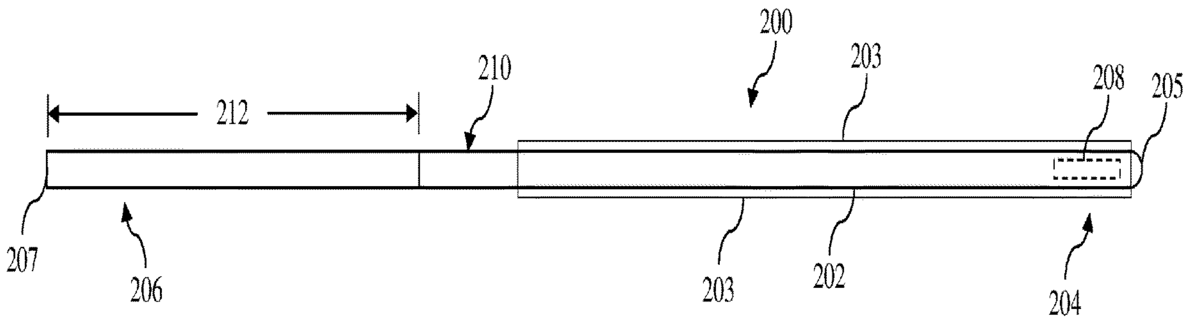
FIG. 3 is a diagrammatic, schematic side view of a sensing guide wire according to an embodiment of the present disclosure.

Referring now to FIG. 3, shown therein is an intravascular device 200 according to an embodiment of the present disclosure. In that regard, the intravascular device 200 includes a flexible elongate member 202 having a distal portion 204 adjacent a distal tip 205 and a proximal portion 206 adjacent a proximal end 207. In that regard, the coating 203 is in contact with or adhered to an external portion of the flexible elongate member 202 to provide the intravascular device 200 with a lubricious external surface having high or increased lubricity. The coating 203 can be positioned along a portion, portions, and/or all of the intravascular device 200. For example, in some instances the coating 203 is positioned on portions of the intravascular device 200 that are intended to have increased lubricity.

A component 208 is positioned within the distal portion 204 of the flexible elongate member 202 proximal of the distal tip 205. Generally, the component 208 is representative of one or more electronic, optical, or electro-optical components. In that regard, the component 208 is a pressure sensor, a flow sensor, a temperature sensor, an imaging element, an optical fiber, an ultrasound transducer, a reflector, a mirror, a prism, an ablation element, an RF electrode, a conductor, and/or combinations thereof. The specific type of component or combination of components can be selected based on an intended use of the intravascular device. In some instances, the component 208 is positioned less than 10 cm, less than 5, or less than 3 cm from the distal tip 205. In some instances, the component 108 is positioned within a housing of the flexible elongate member 202. In that regard, the housing is a separate component secured to the flexible elongate member 202 in some instances. In other instances, the housing is integrally formed as a part of the flexible elongate member 202.

The intravascular device 200 also includes a connector 210 adjacent the proximal portion 206 of the device. In that regard, the connector 210 is spaced from the proximal end 207 of the flexible elongate member 202 by a distance 212. Generally, the distance 212 is between 0% and 50% of the total length of the flexible elongate member 202. While the total length of the flexible elongate member can be any length, in some embodiments the total length is between about 1300 mm and about 4000 mm, with some specific embodiments have a length of 1400 mm, 1900 mm, and 3000 mm. Accordingly, in some instances the connector 210 is positioned at the proximal end 207. In other instances, the connector 210 is spaced from the proximal end 207. For example, in some instances the connector 210 is spaced from the proximal end 207 between about 0 mm and about 1400 mm. In some specific embodiments, the connector 210 is spaced from the proximal end by a distance of 0 mm, 300 mm, and 1400 mm.

The connector 210 is configured to facilitate communication between the intravascular device 200 and another device. More specifically, in some embodiments the connector 210 is configured to facilitate communication of data obtained by the component 208 to another device, such as a computing device or processor. Accordingly, in some embodiments the connector 210 is an electrical connector. In such instances, the connector 210 provides an electrical connection to one or more electrical conductors that extend along the length of the flexible elongate member 202 and are electrically coupled to the component 208. In some embodiments the electrical conductors are embedded within a core of the flexible elongate member. In other embodiments, the connector 210 is an optical connector. In such instances, the connector 210 provides an optical connection to one or more optical communication pathways (e.g., fiber optic cable) that extend along the length of the flexible elongate member 202 and are optically coupled to the component 208. Similarly, in some embodiments the optical fibers are embedded within a core of the flexible elongate member. Further, in some embodiments the connector 210 provides both electrical and optical connections to both electrical conductor(s) and optical communication pathway(s) coupled to the component 208. In that regard, it should be noted that component 208 is comprised of a plurality of elements in some instances. The connector 210 is configured to provide a physical connection to another device, either directly or indirectly. In some instances, the connector 210 is configured to facilitate wireless communication between the intravascular device 200 and another device. Generally, any current or future developed wireless protocol(s) may be utilized. In yet other instances, the connector 210 facilitates both physical and wireless connection to another device.

As noted above, in some instances the connector 210 provides a connection between the component 208 of the intravascular device 200 and an external device. Accordingly, in some embodiments one or more electrical conductors, one or more optical pathways, and/or combinations thereof extend along the length of the flexible elongate member 202 between the connector 210 and the component 208 to facilitate communication between the connector 210 and the component 208. In some instances, at least one of the electrical conductors and/or optical pathways is embedded within the core of the flexible elongate member 202, as described in U.S. Provisional Patent Application No.

61/935,113, filed Feb. 3, 2014, which is hereby incorporated by reference in its entirety. Generally, any number of electrical conductors, optical pathways, and/or combinations thereof can extend along the length of the flexible elongate member 202 between the connector 210 and the component 208, embedded in the core or not. In some instances, between one and ten electrical conductors and/or optical pathways extend along the length of the flexible elongate member 202 between the connector 210 and the component 208. The number of communication pathways and the number of electrical conductors and optical pathways extending along the length of the flexible elongate member 202 is determined by the desired functionality of the component 208 and the corresponding elements that define component 208 to provide such functionality.

Figure 4:
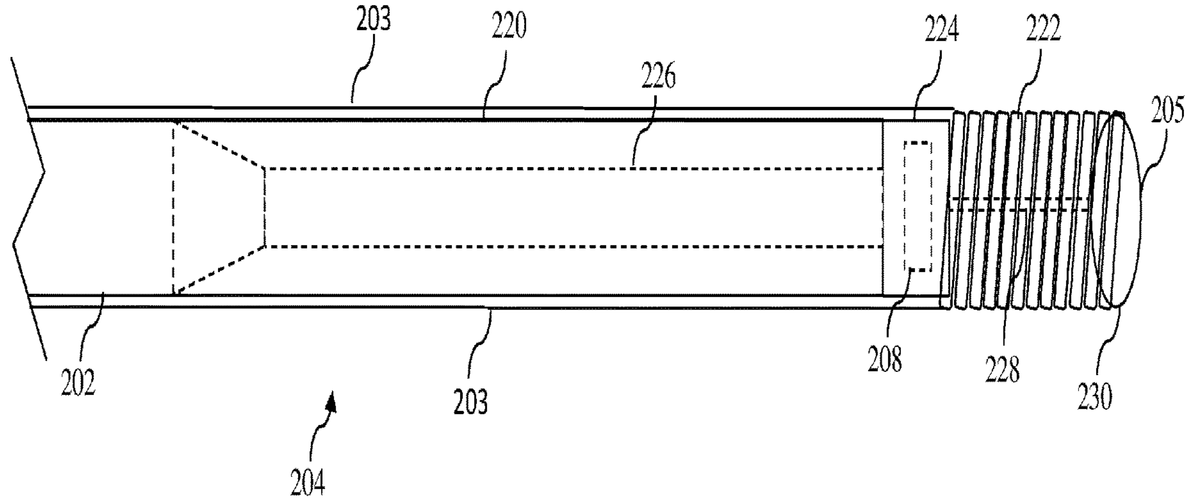
FIG. 4 is a diagrammatic, schematic side view of a distal portion of the sensing guide wire of FIG. 3 according to an embodiment of the present disclosure.
Figure 5:
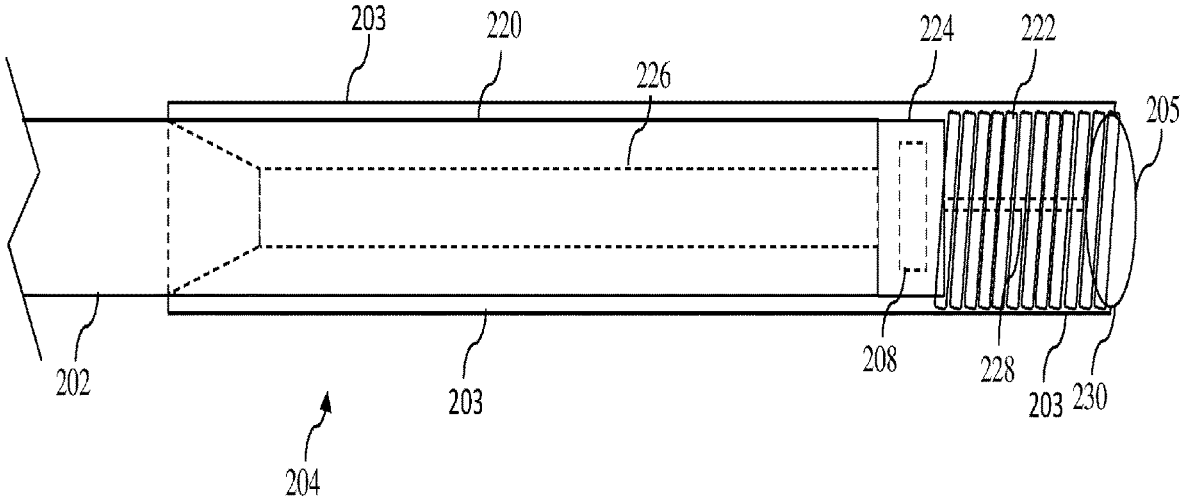
FIG. 5 is a diagrammatic, schematic side view of a distal portion of the sensing guide wire of FIG. 3 according to an embodiment of the present disclosure.

Referring now to FIGS. 4 and 5, shown therein are examples of implementations of the coating 203 on the intravascular device 200 according to the present disclosure. In particular, each of FIGS. 4 and 5 provide a diagrammatic, schematic side view of the distal portion 204 of the intravascular device 200. As shown, the distal portion 204 includes a proximal flexible element 220 and a distal flexible element 222 on each side of a housing 224 containing component 208. A core member 226 extends through the proximal flexible element 220. Similarly, a core member 228 extends through the distal flexible element 222. In some implementations, the core members 226 and 228 are an integral component (i.e., the core member 226 extends through the housing 224 and to define core member 228). Generally, the core members 226, 228 are sized, shaped, and/or formed out of particular material(s) to create a desired mechanical performance for the distal portion 204 of the intravascular device 200. In that regard, in some instances the core member 228 is coupled to a shaping ribbon. For example, in some particular implementations the core member 228 is coupled to a shaping ribbon utilizing a multi-flat transition as described in U.S. Provisional Patent Application No. 62/027,556, filed Jul. 22, 2014, which is hereby incorporated by reference in its entirety.

The proximal and distal flexible elements 220, 222 can be any suitable flexible element, including coils, polymer tubes, and/or coil-embedded polymer tubes. In the illustrated embodiment the proximal flexible element 220 is a coil-embedded polymer tube and the distal flexible element 222 is a coil. As discussed in greater detail below, the proximal and/or distal flexible elements 220, 222 are at least partially filled with one or more flexible adhesives to improve the mechanical performance and durability of the intravascular device 200. In that regard, in some instances adhesives with varying degrees of durometer are utilized to provide a desired transition in bending stiffness along the length of the intravascular device 200. A solder ball 230 or other suitable element is secured to the distal end of the distal flexible element 222. As shown, the solder ball 230 defines the distal tip 205 of the intravascular device 200 with an atraumatic tip suitable for advancement through patient vessels, such as vasculature. In some embodiments, a flow sensor is positioned at the distal tip 205 instead of the solder ball 230.

FIG. 4 illustrates an embodiment where the coating 203 extends along a majority of the length of the intravascular device 200, including along the flexible elongate member 202 (e.g., along all, a majority, and/or a portion of the distance between the connector 210 and the proximal flexible element 220 in some instances) and along the proximal flexible element 220 to the distal flexible element 222. However, in FIG. 4, the coating 203 does not extend over the distal flexible element 222. FIG. 5 illustrates another embodiment where the coating extends along the proximal flexible element 220 and the distal flexible element 222. However, in the embodiment of FIG. 5 at least the distal portion of the flexible elongate member 202 does not include the coating 203. It is understood that the coating 203 may be applied to any combination of areas and/or components of the intravascular device 200, including in the axial (along the length of the device) and/or circumferential (around the circumference of the device) directions. For example, the coating 203 may be applied partially around the circumference of the device (e.g., half, ¼, ¾, or other suitable amount) in certain areas.

The distal portion 204 of the intravascular device 200—as well as the proximal portion 206 and the flexible elongate member 202—may be formed using any suitable approach so long as a portion of the intravascular device is coated with coating 203 in accordance with the present disclosure. Accordingly, in some implementations the intravascular device 200 includes features similar to the distal, intermediate, and/or proximal sections described in one or more of U.S. Pat. Nos. 5,125,137, 5,873,835, 6,106,476, 6,551,250, U.S. patent application Ser. No. 13/931,052, filed Jun. 28, 2013, U.S. patent application Ser. No. 14/135,117, filed Dec. 19, 2013, U.S. patent application Ser. No. 14/137,364, filed Dec. 20, 2013, U.S. patent application Ser. No. 14/139,543, filed Dec. 23, 2013, U.S. patent application Ser. No. 14/143,304, filed Dec. 30, 2013, and U.S. Provisional Patent Application No. 61/935,113, filed Feb. 3, 2014, each of which is hereby incorporated by reference in its entirety.

Figure 6:
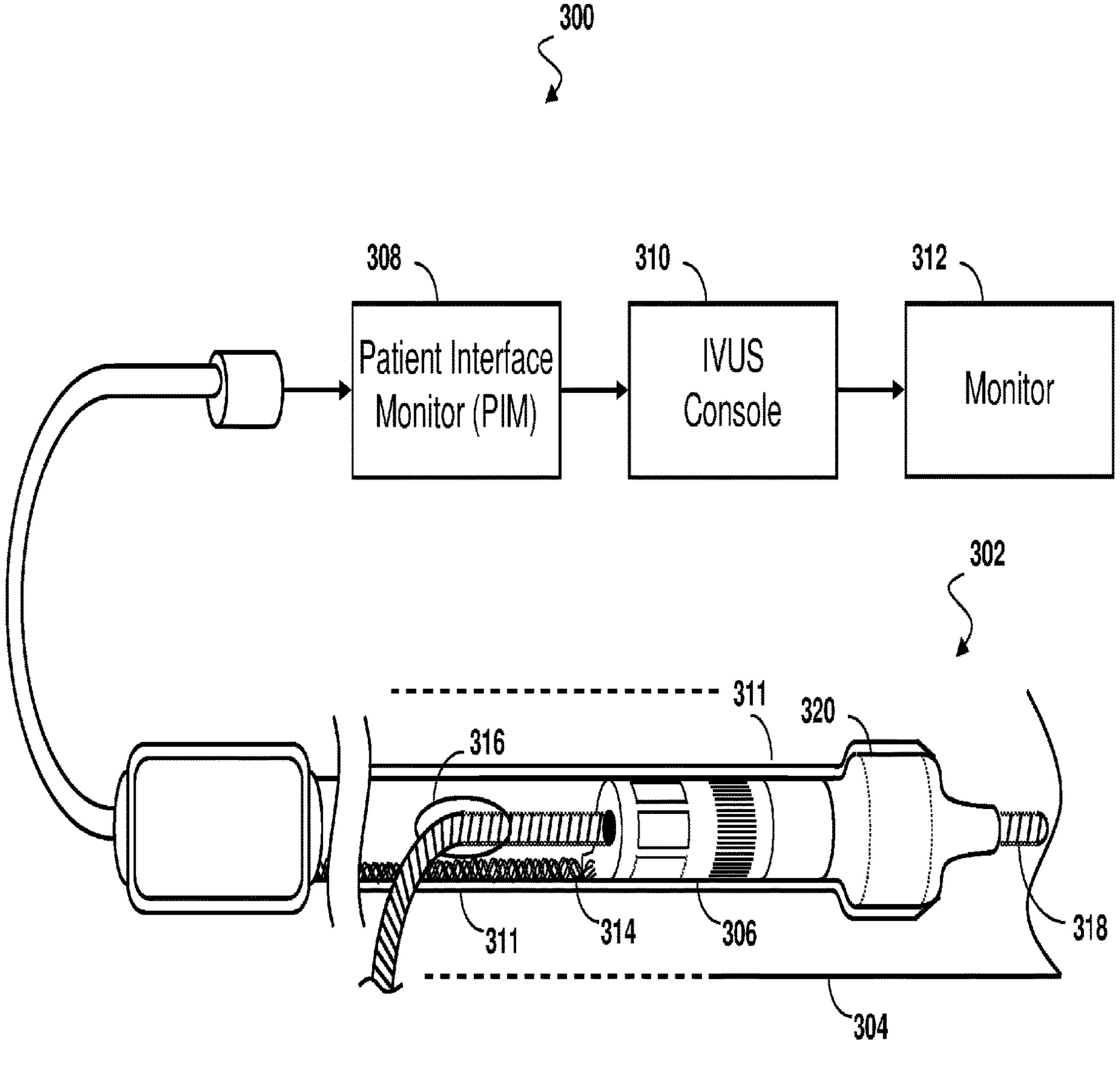
FIG. 6 is a diagrammatic schematic view of an intravascular ultrasound (IVUS) imaging system according to an embodiment of the present disclosure.

FIG. 6 is a diagrammatic schematic view of an ultrasound imaging system 300 according to an embodiment of the present disclosure. The distal-most end of the elongate member 302 includes a scanner assembly 306 with an array of ultrasound transducers and associated control circuitry. When the scanner assembly 306 is positioned near the area to be imaged, the ultrasound transducers are activated and ultrasonic energy is produced. A portion of the ultrasonic energy is reflected by the vessel 304 and the surrounding anatomy and received by the transducers. Corresponding echo information is passed along through a Patient Interface Monitor (PIM) 308 to an IVUS console 310, which renders the information as an image for display on a monitor 312.

The imaging system 300 may use any of a variety of ultrasonic imaging technologies. Accordingly, in some embodiments of the present disclosure, the IVUS imaging system 300 is a solid-state IVUS imaging system incorporating an array of piezoelectric transducers fabricated from lead-zirconate-titanate (PZT) ceramic. In some embodiments, the system 300 incorporates capacitive micromachined ultrasonic transducers (CMUTs), or piezoelectric micromachined ultrasound transducers (PMUTs).

In some embodiments, the IVUS system 300 includes some features similar to traditional solid-state IVUS system, such as the EagleEye® catheter available from Volcano Corporation and those disclosed in U.S. Pat. No. 7,846,101 hereby incorporated by reference in its entirety. For example, the elongate member 302 includes the ultrasound scanner assembly 306 at a distal end of the member 302, which is coupled to the PIM 308 and the IVUS console 310 by a cable 314 extending along the longitudinal body of the member 302. The cable 314 caries control signals, echo data, and power between the scanner assembly 306 and the remainder of the IVUS system 300. In some instances, the scanner assembly 306 is transitioned from a flat configuration to a rolled or more cylindrical configuration. For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND TRANSDUCER ASSEMBLY HAVING A FLEXIBLE SUBSTRATE," each of which is hereby incorporated by reference in its entirety.

In an embodiment, the elongate member 302 further includes a guide wire exit port 316. The guide wire exit port 316 allows a guide wire 318 to be inserted towards the distal end in order to direct the member 302 through a vascular structure (i.e., a vessel) 304. Accordingly, in some instances the IVUS device is a rapid-exchange catheter. In an embodiment, the elongate member 302 also includes an inflatable balloon portion 320 near the distal tip. The balloon portion 320 is open to a lumen that travels along the length of the IVUS device and ends in an inflation port (not shown). The balloon 320 may be selectively inflated and deflated via the inflation port.

The PIM 308 facilitates communication of signals between the IVUS console 310 and the elongate member 302 to control the operation of the scanner assembly 306. This includes generating control signals to configure the scanner, generating signals to trigger the transmitter circuits, and/or forwarding echo signals captured by the scanner assembly 306 to the IVUS console 310. With regard to the echo signals, the PIM 308 forwards the received signals and, in some embodiments, performs preliminary signal processing prior to transmitting the signals to the console 310. In examples of such embodiments, the PIM 308 performs amplification, filtering, and/or aggregating of the data. In an embodiment, the PIM 308 also supplies high- and low-voltage DC power to support operation of the circuitry within the scanner assembly 306.

The IVUS console 310 receives the echo data from the scanner assembly 306 by way of the PIM 308 and processes the data to create an image of the tissue surrounding the scanner assembly 306. The console 310 may also display the image on the monitor 312.

The ultrasound imaging system 300 may be utilized in a variety of applications and can be used to image vessels and structures within a living body. Vessel 304 represents fluid filled or surrounded structures, both natural and man-made, within a living body that may be imaged and can include for example, but without limitation, structures such as: organs including the liver, heart, kidneys, as well as valves within the blood or other systems of the body. In addition to imaging natural structures, the images may also include imaging man-made structures such as, but without limitation, heart valves, stents, shunts, filters and other devices positioned within the body.

In accordance with the present disclosure, a coating 311 is applied to at least a portion of the elongate member 302. In this regard, the coating 311 is in contact with or adhered to an external surface of an elongate member 302 to facilitate introduction of the elongate member 302 into a vessel 304 and/or removal of the elongate member 302 from the vessel 304. It is understood that the coating 311 may be applied to any combination of areas and/or components of the elongate member 302, including in the axial (along the length of the device) and/or circumferential (around the circumference of the device) directions. For example, the coating 311 may be applied partially around the circumference of the device (e.g., half, ¼, ¾, or other suitable amount) in certain areas.

Figure 7:
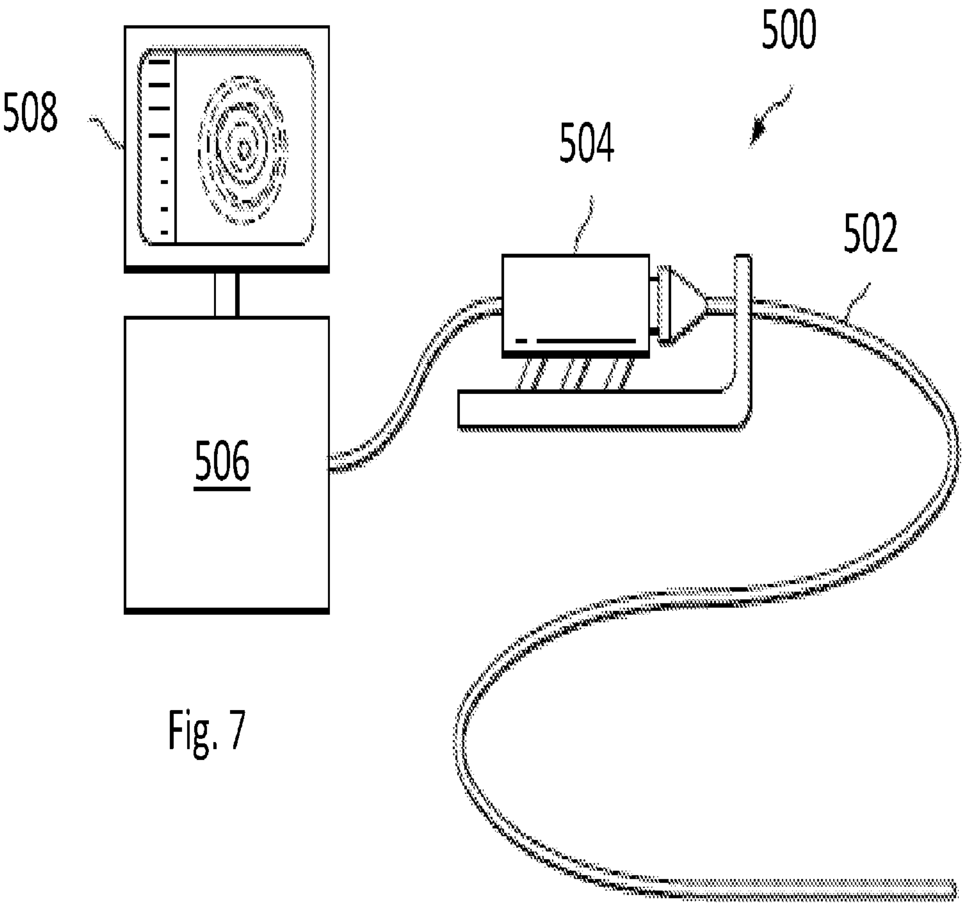
FIG. 7 is a diagrammatic schematic view of an imaging system according to an embodiment of the present disclosure.

Referring to FIG. 7, shown therein is an IVUS imaging system 500 according to an embodiment of the present disclosure. In some embodiments of the present disclosure, the IVUS imaging system 500 is a lead-zirconate-titanate (PZT) or piezoelectric micro-machined ultrasound transducer (PMUT) rotational IVUS imaging system. For brevity, the following description will utilize a PMUT rotational IVUS imaging system for illustrative purposes only.

In that regard, the main components of the PMUT rotational IVUS imaging system are the PMUT rotational IVUS catheter 502, a PMUT catheter compatible patient interface module (PIM) 504, an IVUS console or processing system 506, and a monitor 508 to display the IVUS images generated by the IVUS console 506.

Figure 8:
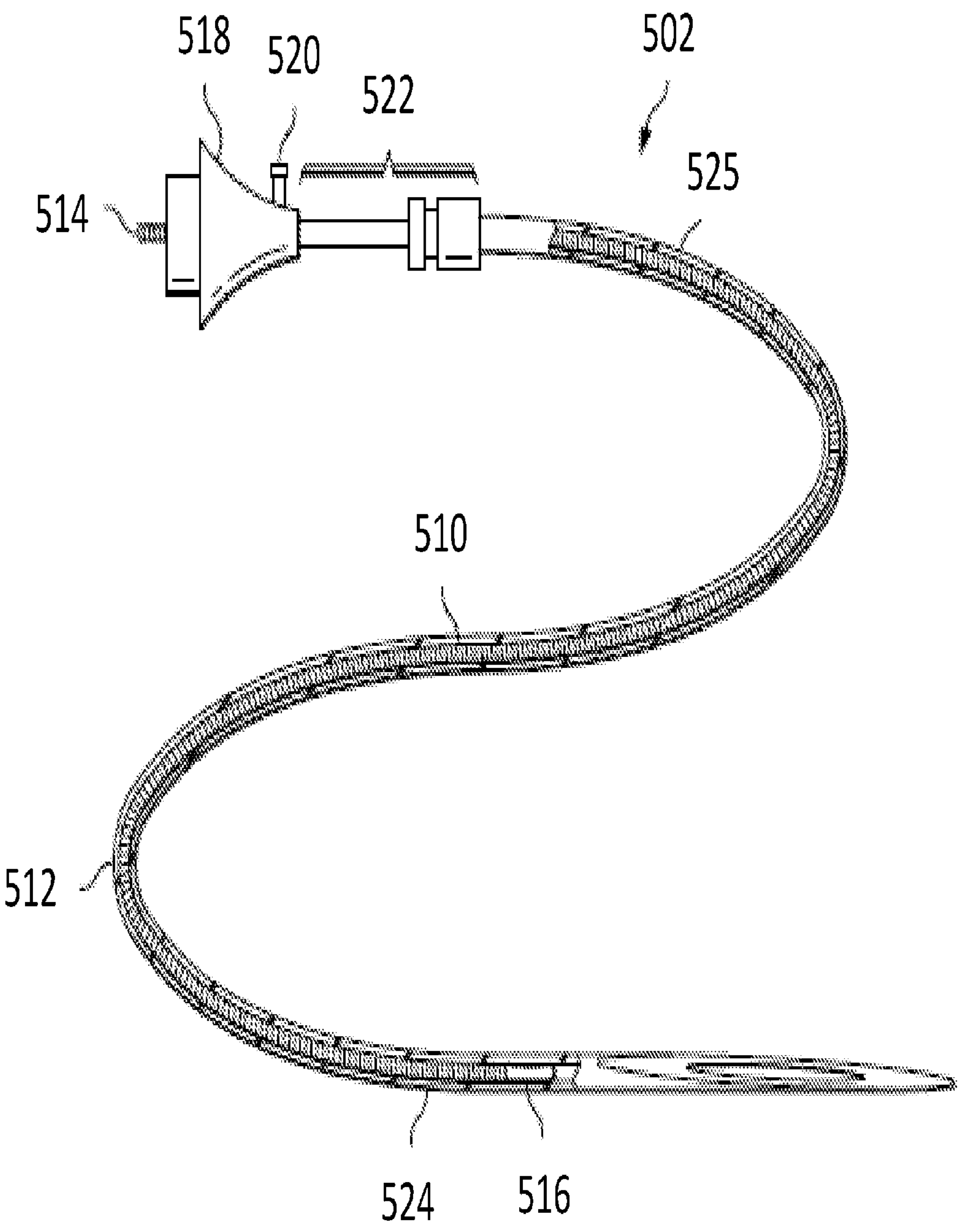
FIG. 8 is a diagrammatic, partial cutaway perspective view of an imaging device according to an embodiment of the present disclosure.

Referring now to FIG. 8, shown therein is a diagrammatic, partial cutaway perspective view of the PMUT catheter 502 according to an embodiment of the present disclosure. In that regard, FIG. 8 shows additional detail regarding the construction of the PMUT rotational IVUS catheter 502. In many respects, this catheter is similar to traditional rotational IVUS catheters, such as the Revolution® catheter available from Volcano Corporation and described in U.S. Pat. No. 8,104,479, or those disclosed in U.S. Pat. Nos. 5,243,988 and 5,546,948, each of which is hereby incorporated by reference in its entirety. In that regard, the PMUT rotational IVUS catheter 502 includes an imaging core 510 and an outer catheter/sheath assembly 512. The imaging core 510 includes a flexible drive shaft that is terminated at the proximal end by a rotational interface 514 providing electrical and mechanical coupling to the PIM 504 of FIG. 7. The distal end of the flexible drive shaft of the imaging core 510 is coupled to a transducer housing 516 containing the PMUT and associated circuitry. The catheter/sheath assembly 512 includes a hub 518 that supports the rotational interface and provides a bearing surface and a fluid seal between the rotating and non-rotating elements of the catheter assembly. The hub 518 includes a Luer lock flush port 520 through which saline is injected to flush out the air and fill the inner lumen of the sheath with an ultrasound-compatible fluid at the time of use of the catheter. The saline or other similar flush is typically required since ultrasound does not readily propagate through air. Saline also provides a biocompatible lubricant for the rotating driveshaft. The hub 518 is coupled to a telescope 522 that includes nested tubular elements and a sliding fluid seal that permit the catheter/sheath assembly 512 to be lengthened or shortened to facilitate axial movement of the transducer housing within an acoustically transparent window 524 of the distal portion of the catheter 502. In some embodiments, the window 524 is composed of thin-walled plastic tubing fabricated from material(s) that readily conduct ultrasound waves between the transducer and the vessel tissue with minimal attenuation, reflection, or refraction. A proximal shaft 525 of the catheter/sheath assembly 512 bridges the segment between the telescope 522 and the window 524, and is composed of a material or composite that provides a lubricious internal lumen and optimum stiffness, but without the need to conduct ultrasound.

Figure 9:
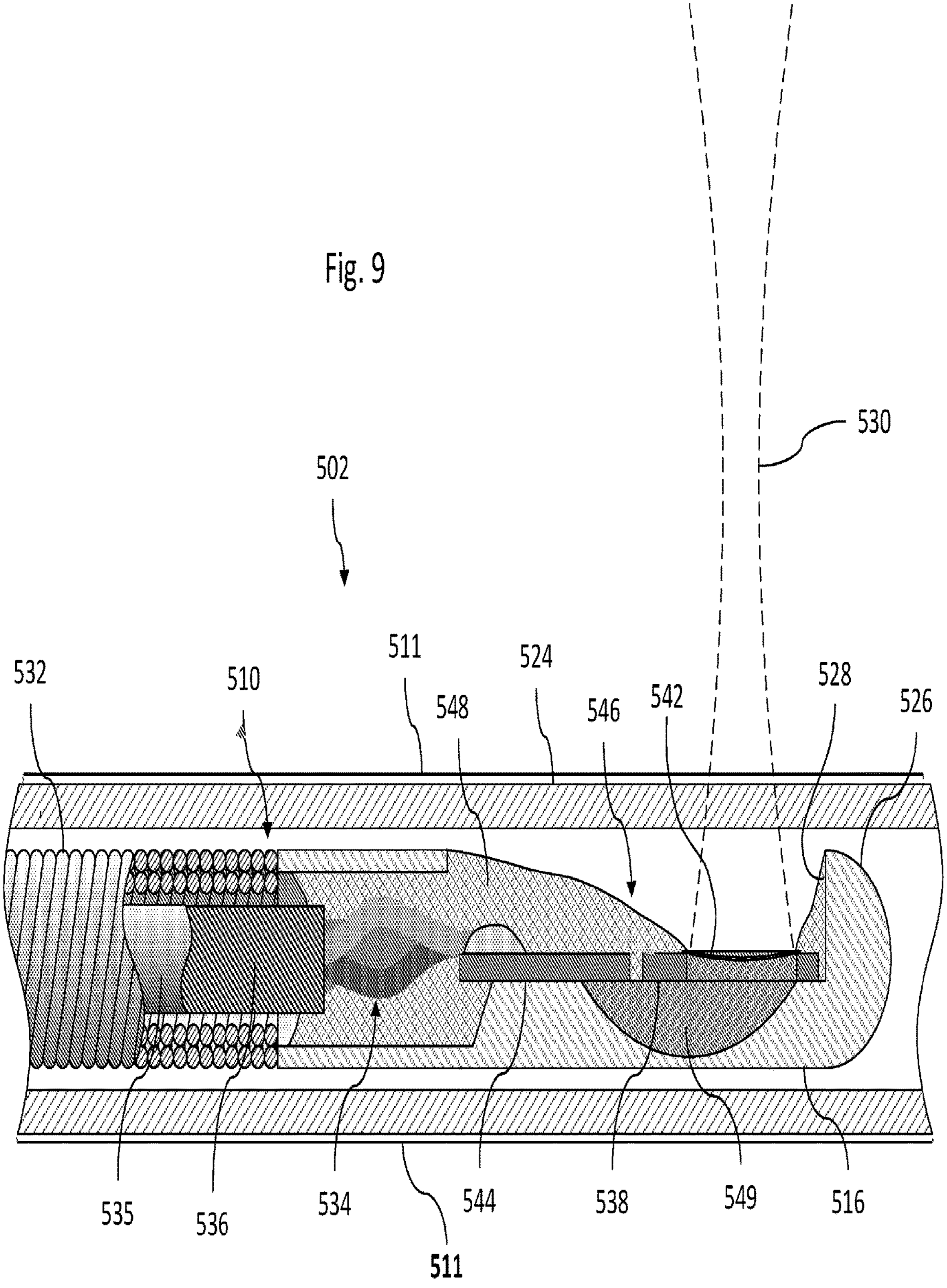
FIG. 9 is a diagrammatic, cross-sectional side view of a distal portion of an imaging device according to an embodiment of the present disclosure.

Referring now to FIG. 9, shown therein is a cross-sectional side view of a distal portion of the catheter 502 according to an embodiment of the present disclosure. FIG. 9 shows an expanded view of aspects of the distal portion of the imaging core 510. In this exemplary embodiment, the imaging core 510 is terminated at its distal tip by a housing 516 fabricated from stainless steel and provided with a rounded nose 526 and a cutout 528 for the ultrasound beam 530 to emerge from the housing 516. In some embodiments, the flexible driveshaft 532 of the imaging core 510 is composed of two or more layers of counter wound stainless steel wires, welded, or otherwise secured to the housing 516 such that rotation of the flexible driveshaft also imparts rotation on the housing 516. In the illustrated embodiment, the ASIC 544 and the MEMS 538 components are wire-bonded and glued together to form an ASIC/MEMS hybrid assembly 546, which is mounted to the transducer housing 516 and secured in place with epoxy 548. The leads of the multi-conductor electrical cable 534 with optional shield 536 and jacket 535 are soldered or otherwise electrically coupled directly to the ASIC 144 in this embodiment. The electrical cable 534 extends through an inner lumen of the flexible driveshaft 532 to the proximal end of the imaging core 510 where it is terminated to the electrical connector portion of the rotational interface 114.

When assembled together, as shown in FIG. 9, the PMUT MEMS 538 and the ASIC 544 form an ASIC/MEMS hybrid assembly 546 that is mounted within the housing 516, with the ASIC 544 electrically coupled to the PMUT MEMS 538 through two or more connections such as wire bonds. In that regard, in some embodiments of the present disclosure the ASIC 544 includes an amplifier, a transmitter, and a protection circuit associated with the PMUT MEMS as discussed above. The PMUT MEMS 538 includes a spherically focused ultrasound transducer 542. In the illustrated embodiment, the connections between the ASIC 544 and MEMS 538 are provided by wire bonds, while in other embodiments, the ASIC 544 is flip-chip mounted to the substrate of the PMUT MEMS 538 using anisotropic conductive adhesive or suitable alternative chip-to-chip bonding method. In still other embodiments, both ASIC 544 and MEMS 538 components are attached to a flexible circuit substrate which includes conductive paths to electrically connect the two components.

In accordance with the present disclosure, a coating 511 is applied to at least a portion of the IVUS catheter. In this regard, the coating 511 is in contact with or adhered to an external surface of the catheter 512 to facilitate introduction of the catheter 512 into a vessel and/or removal of the catheter 512 from the vessel. In the illustrated embodiment, the coating 511 is in contact with or adhered to the exterior portion of the catheter 512 along at least a distal portion of the device, including over the window 524. In other embodiments, the coating 511 does not extend over the window 524. However, it is understood that the coating 511 may be applied to any combination of areas and/or components of the IVUS catheter, including in the axial (along the length of the device) and/or circumferential (around the circumference of the device) directions. For example, the coating 511 may be applied partially around the circumference of the device (e.g., half, ¼, ¾, or other suitable amount) in certain areas.

While the present invention has been described in terms of certain embodiments, those of ordinary skill in the art will recognize that the invention can be practiced with modification within the spirit and scope of the appended claims.

Any spatial references such as, for example, "upper," "lower," "above," "below," "between," "bottom," "vertical," "horizontal," "angular," "upwards," "downwards," "side-to-side," "left-to-right," "left," "right," "right-to-left," "top-to-bottom," "bottom-to-top," "top," "bottom," "bottom-up," "top-down," etc., are for the purpose of illustration only and do not limit the specific orientation or location of the structure described above.

The following examples are illustrative of the compositions and methods discussed above.

EXAMPLES

A primer layer mixture was prepared by dissolving the ingredients listed in Table 1 into isopropyl alcohol (IPA). A top coating layer mixture was prepared by dissolving the ingredients listed in Table 2 into ethanol. A customized hydrophilic coater with a UV curing chamber built by Martek Automation was used to coat and polymerize the primer layer mixture directly onto a section of an Eagle Eye® Platinum IVUS catheter. Then, the same hydrophilic coater was used to coat and polymerize the top coating layer mixture onto the cured primer layer to form the samples of Example 1. The samples of Example 2 were prepared using the same steps as Example 1, followed by subjecting the samples to an aging process that simulated one year of aging at DDL Inc. (Distribution Dynamic Labs), Fountain Valley, Calif. The conditions for 1-year aging are 55° C.±2° C. @<20% RH for 38 days. Comparative Example samples were prepared by using the hydrophilic coater to coat and polymerize DSM Comfortcoat® onto a section of an Eagle Eye® Platinum IVUS catheter. Three samples sets, "Aging T=0," "Aging T=1 Year Accelerated," and "DSM control," containing ten samples each, were prepared according to the method used to prepare the samples of Example 1, Example 2, or the Comparative Example, respectively.

TABLE 1

| Ingredients | Amount (g) |
|---|---|
| Trimethylolpropane Triacrylate | 43.2 |
| Photomer ® 4173 | 43.2 |
| 2,2-Dimethoxy-2-phenylacetophenone | 0.86 |
| Benzophenone | 0.86 |

TABLE 2

| Ingredients | Amount (g) |
|---|---|
| BASF Luvitec ® K 90 Powder | 81.0 |
| Photomer ® 4173 | 3.33 |
| N,N-Dimethylacrylamide | 15.0 |
| 1-Vinyl-2-pyrrolidone | 6.0 |
| 2,2-Dimethoxy-2-phenylacetophenone | 0.12 |
| Benzophenone | 0.12 |

Figure 2:
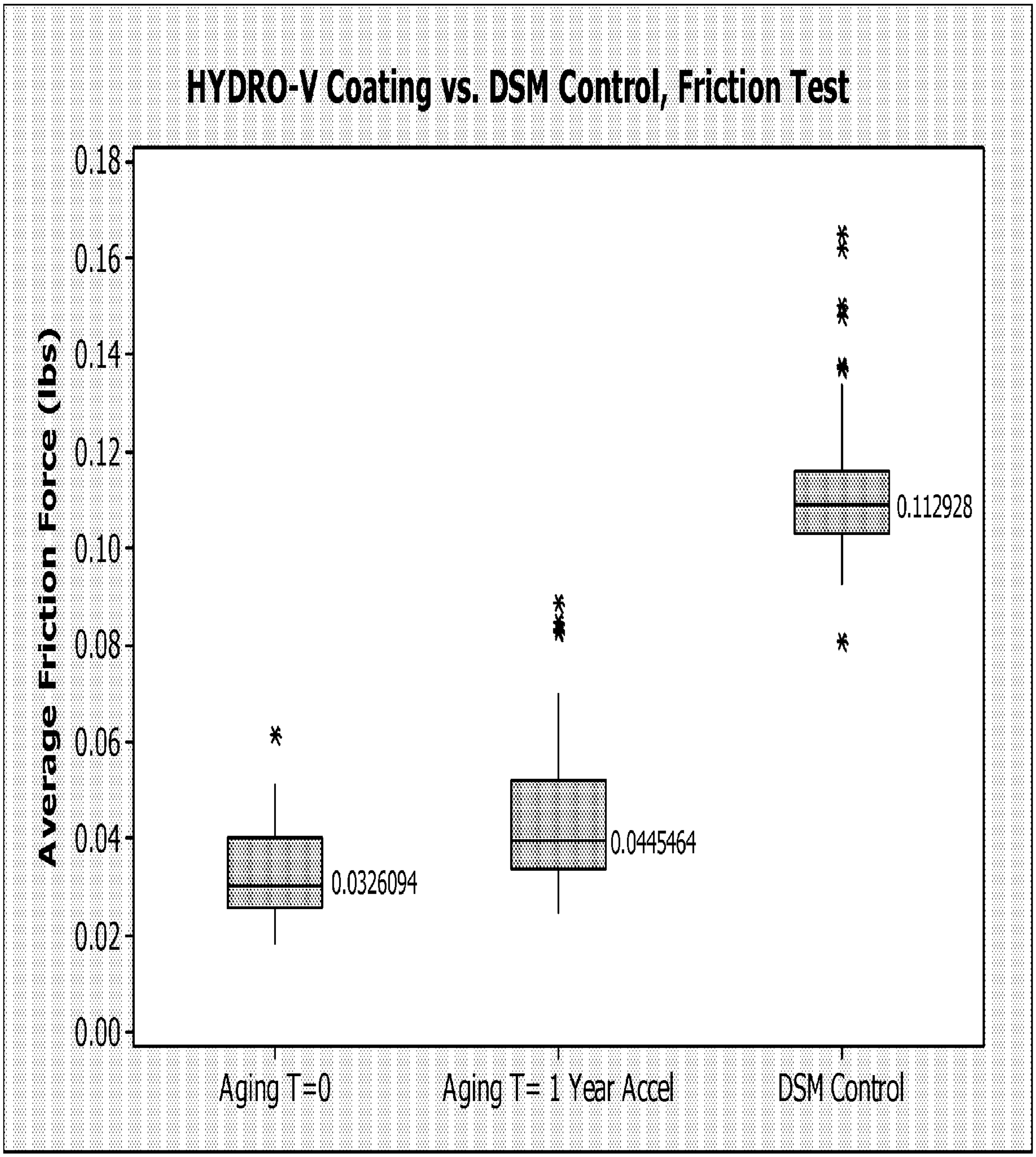
FIG. 2 exhibits a plot of average friction force as a function of aging.

The friction force of each sample of Example 1, Example 2, and the Comparative Example was measured using an INSTRON® model #3343 tester with a 10 newton load cell and pig aorta as friction pads in a room temperature water bath. The average friction force was calculated to be 0.032094 lbf for the Aging T=0 sample set, 0.00445464 lbf for the T=1 year accelerated aging sample set, and 0.112928 lbf for the DSM control (DSM Comfortcoat®) coated sample set, as shown in FIG. 2. The experimental results indicated that the lubricious coating in the Example 2 has a lower friction surface than the surface of the Comparative Example coating even after 1 year of accelerated aging.

While the present invention has been described in terms of certain embodiments, those of ordinary skill in the art will recognize that the invention can be practiced with modification within the spirit and scope of the appended claims.

The present disclosure has been described relative to certain embodiments. Improvements or modifications that become apparent to persons of ordinary skill in the art only after reading this disclosure are deemed within the spirit and scope of the application. It is understood that several modifications, changes and substitutions are intended in the foregoing disclosure and in some instances some features of the invention will be employed without a corresponding use of other features. Accordingly, it is appropriate that the appended claims be construed broadly and in a manner consistent with the scope of the invention.

What is claimed is:

1. An intravascular device, comprising:

a flexible elongate member;

an outer coating disposed over at least a portion of the flexible elongate member, wherein the outer coating comprises:

a primer layer in contact with the at least a portion of the flexible elongate member, wherein the primer layer comprises a monomer with carboxylic acid groups; and a top coating layer different from the primer layer, wherein the top coating layer is disposed over and in contact with the primer layer, wherein the top coating layer is an outermost layer of the outer coating, wherein the top coating layer comprises a hydrophilic polymer and a monomer, wherein the monomer of the primer layer is a network forming monomer capable of crosslinking the primer layer, wherein the monomer of the primer layer is a multifunctional acrylate, and wherein the multifunctional acrylate comprises at least one of trimethylolpropane triacrylate or trimethylolpropane ethoxylate triacrylate.

2. An intravascular device, comprising:

a flexible elongate member;

an outer coating disposed over at least a portion of the flexible elongate member, wherein the outer coating comprises:

a primer layer in contact with the at least a portion of the flexible elongate member, wherein the primer layer comprises a monomer with carboxylic acid groups; and a top coating layer different from the primer layer, wherein the top coating layer is disposed over and in contact with the primer layer, wherein the top coating layer is an outermost layer of the outer coating, wherein the top coating layer comprises a hydrophilic polymer and a monomer, wherein the monomer of the primer layer is a network forming monomer capable of crosslinking the primer layer, wherein the monomer of the primer layer is a multifunctional acrylate, wherein the primer layer further comprises an acid functionalized monoacrylate, and wherein a ratio of the multifunctional acrylate to the acid functionalized monoacrylate is from about 5:1 to about 1:5.

3. The intravascular device of claim 1, wherein the hydrophilic polymer comprises polyvinylpyrrolidone.

4. An intravascular device, comprising:

a flexible elongate member;

an outer coating disposed over at least a portion of the flexible elongate member, wherein the outer coating comprises:

a primer layer in contact with the at least a portion of the flexible elongate member, wherein the primer layer comprises a monomer with carboxylic acid groups; and a top coating layer different from the primer layer, wherein the top coating layer is disposed over and in contact with the primer layer, wherein the top coating layer is an outermost layer of the outer coating, and wherein the top coating layer comprises a hydrophilic polymer and a monomer, wherein the monomer of the top coating layer comprises a hydrophilic monomer that immobilizes the hydrophilic polymer.

5. The intravascular device of claim 4, wherein the hydrophilic monomer is selected from the group consisting of 1-vinyl-2-pyrrolidone, N,N-dimethylacrylamide, or combinations thereof.

6. The intravascular device of claim 1, wherein the monomer of the top coating layer comprises an acid functionalized monoacrylate.

7. The intravascular device of claim 1, wherein the primer layer further comprises a first polymerization initiator, and wherein the top coating layer further comprises a second polymerization initiator.

8. The intravascular device of claim 7, wherein at least one of the first polymerization initiator or the second polymerization initiator is selected from the group consisting of a thermal initiator, a redox initiator, or a photoinitiator.

9. The intravascular device of claim 7, wherein at least one of the first polymerization initiator or the second polymerization initiator is a photoinitiator.

10. The intravascular device of claim 2, wherein the hydrophilic polymer comprises polyvinylpyrrolidone.

11. The intravascular device of claim 4, wherein the hydrophilic polymer comprises polyvinylpyrrolidone.

12. The intravascular device of claim 2, wherein the monomer of the top coating layer comprises an acid functionalized monoacrylate.

13. The intravascular device of claim 4, wherein the monomer of the top coating layer comprises an acid functionalized monoacrylate.

14. The intravascular device of claim 2, wherein the primer layer further comprises a first polymerization initiator, and wherein the top coating layer further comprises a second polymerization initiator.

15. The intravascular device of claim 14, wherein at least one of the first polymerization initiator or the second polymerization initiator is selected from the group consisting of a thermal initiator, a redox initiator, or a photoinitiator.

16. The intravascular device of claim 14, wherein at least one of the first polymerization initiator or the second polymerization initiator is a photoinitiator.

17. The intravascular device of claim 4, wherein the primer layer further comprises a first polymerization initiator, and wherein the top coating layer further comprises a second polymerization initiator.

18. The intravascular device of claim 17, wherein at least one of the first polymerization initiator or the second polymerization initiator is selected from the group consisting of a thermal initiator, a redox initiator, or a photoinitiator.

19. The intravascular device of claim 17, wherein at least one of the first polymerization initiator or the second polymerization initiator is a photoinitiator.

20. The intravascular device of claim 4, wherein the monomer of the primer layer is a network forming monomer capable of crosslinking the primer layer.

21. The intravascular device of claim 20, wherein the monomer of the primer layer is a multifunctional acrylate.

22. The intravascular device of claim 21, wherein the multifunctional acrylate comprises at least one of trimethylolpropane triacrylate or trimethylolpropane ethoxylate triacrylate.

23. The intravascular device of claim 21, wherein the primer layer further comprises an acid functionalized monoacrylate.

24. The intravascular device of claim 23, wherein a ratio of the multifunctional acrylate to the acid functionalized monoacrylate is from about 5:1 to about 1:5.

25. The intravascular device of claim 2, wherein the multifunctional acrylate comprises at least one of trimethylolpropane triacrylate or trimethylolpropane ethoxylate triacrylate.

26. The intravascular device of claim 1, wherein the primer layer further comprises an acid functionalized monoacrylate.

27. The intravascular device of claim 26, wherein a ratio of the multifunctional acrylate to the acid functionalized monoacrylate is from about 5:1 to about 1:5.

28. The intravascular device of claim 1, wherein the monomer of the top coating layer comprises a hydrophilic monomer that immobilizes the hydrophilic polymer.

29. The intravascular device of claim 2, wherein the monomer of the top coating layer comprises a hydrophilic monomer that immobilizes the hydrophilic polymer.

30. The intravascular device of claim 28, wherein the hydrophilic monomer is selected from the group consisting of 1-vinyl-2-pyrrolidone, N,N-dimethylacrylamide, or combinations thereof.

31. The intravascular device of claim 29, wherein the hydrophilic monomer is selected from the group consisting of 1-vinyl-2-pyrrolidone, N,N-dimethylacrylamide, or combinations thereof.

* * * * *